(12) United States Patent
Bor

(10) Patent No.: US 8,409,181 B2
(45) Date of Patent: Apr. 2, 2013

(54) METHODS AND SYSTEMS FOR TREATING PRESBYOPIA

(75) Inventor: Zsolt Bor, San Clemente, CA (US)

(73) Assignee: AMO Development, LLC., Santa Ana, CA (US)

( * ) Notice: Subject to any disclaimer, the term of this patent is extended or adjusted under 35 U.S.C. 154(b) by 757 days.

(21) Appl. No.: 12/612,734

(22) Filed: Nov. 5, 2009

(65) Prior Publication Data

US 2011/0106066 A1     May 5, 2011

(51) Int. Cl.
*A61F 9/007*     (2006.01)
(52) U.S. Cl. .......................... 606/5; 128/898
(58) Field of Classification Search .................. 128/898; 606/4–6
See application file for complete search history.

(56) References Cited

U.S. PATENT DOCUMENTS

| | | |
|---|---|---|
| 4,665,913 A | 5/1987 | L'Esperance |
| 4,669,466 A | 6/1987 | L'Esperance |
| 4,732,148 A | 3/1988 | L'Esperance |
| 4,770,172 A | 9/1988 | L'Esperance |
| 4,773,414 A | 9/1988 | L'Esperance |
| 5,108,388 A | 4/1992 | Trokel |
| 5,144,630 A | 9/1992 | Lin |
| 5,163,934 A | 11/1992 | Munnerlyn |
| 5,207,668 A | 5/1993 | L'Esperance |
| 5,219,343 A | 6/1993 | L'Esperance |
| 5,520,679 A | 5/1996 | Lin |
| 5,533,997 A | 7/1996 | Ruiz |
| 5,646,791 A | 7/1997 | Glockler |
| 5,742,626 A | 4/1998 | Mead et al. |
| 5,782,822 A | 7/1998 | Telfair et al. |
| 5,928,129 A | 7/1999 | Ruiz |
| 6,004,313 A | 12/1999 | Shimmick et al. |
| 6,090,102 A | 7/2000 | Telfair et al. |
| 6,280,435 B1 | 8/2001 | Odrich et al. |
| 6,302,877 B1 | 10/2001 | Ruiz |
| 6,483,787 B1 | 11/2002 | Sugasawa et al. |
| 6,663,619 B2 | 12/2003 | Odrich et al. |
| 6,740,078 B2 | 5/2004 | Tamayo |
| 6,935,808 B1 | 8/2005 | Dempster |
| 6,969,386 B2 | 11/2005 | Tamayo et al. |
| 7,168,807 B2 | 1/2007 | Chernyak et al. |
| 7,261,412 B2 | 8/2007 | Somani et al. |
| 7,293,873 B2 | 11/2007 | Dai et al. |
| 7,320,517 B2 | 1/2008 | Dai et al. |
| 7,413,566 B2 | 8/2008 | Yee |
| 7,419,485 B2 | 9/2008 | Chernyak |
| 7,434,936 B2 | 10/2008 | Dai et al. |
| 7,478,907 B2 | 1/2009 | Somani et al. |

(Continued)

OTHER PUBLICATIONS

Excimer Laser Correction of Presbyopia: The Final Frontier, Tamayo, Techniques in Ophthalmology, 5(3):92-96, 2007.*

(Continued)

*Primary Examiner* — Henry M Johnson, III
(74) *Attorney, Agent, or Firm* — AMO Development, LLC.

(57) ABSTRACT

Methods and systems for treating presbyopia are provided. In accordance with an embodiment, by way of example only, a method of treating presbyopia of an eye includes ablating the stroma to form a final ablated shape in the stroma, the final ablated shape including a central zone defined by a concavity having a central zone depth and a central zone diameter, the central zone depth and the central zone diameter each selected to provide the cornea with a near-vision add power after the epithelium is regenerated over the stroma.

19 Claims, 7 Drawing Sheets

U.S. PATENT DOCUMENTS

| | | |
|---|---|---|
| 2002/0040219 A1 | 4/2002 | Nakamura et al. |
| 2002/0135736 A1 | 9/2002 | Stark et al. |
| 2003/0199858 A1 | 10/2003 | Schelonka |
| 2004/0054356 A1 | 3/2004 | Odrich et al. |
| 2005/0107775 A1 | 5/2005 | Huang et al. |
| 2009/0157061 A1* | 6/2009 | Ruiz et al. .......................... 606/5 |
| 2010/0191229 A1* | 7/2010 | Bille et al. ........................ 606/5 |

OTHER PUBLICATIONS

Correction of Presbyopia by Technovision Central Multifocal LASIK. Alio et al., Journal of Refractive Surgery, vol. 22, May 2006.*

International Search Report for Application No. PCT/US2010/055151, mailed on Jan. 26, 2011, 4 pages.

* cited by examiner

METHODS AND SYSTEMS FOR TREATING PRESBYOPIA

TECHNICAL FIELD

The inventive subject matter relates to optical diagnosis and correction, and in particular provides methods and systems for treating presbyopia.

BACKGROUND

Presbyopia is a condition that affects the accommodation properties of the eye. Generally, as objects move closer to a young, properly functioning eye, ciliary muscle contraction and zonular relaxation allow a crystalline lens of the eye to become rounder or more convex, and thus increase its optical power and ability to focus at near distances. Accommodation can allow the eye to focus and refocus between near and far objects. However, an eye affected by presbyopia often loses the ability to rapidly and easily refocus on objects at varying distances. The ability to focus on objects at near distances may also be lost. Although the condition progresses over the lifetime of an individual, the effects of presbyopia usually become noticeable after the age of 45 years. For example, the crystalline lens may lose a substantial amount of its elastic properties and may have a limited ability to change shape.

To address the vision problems associated with presbyopia, reading glasses have traditionally been used by individuals to add plus optical power to the eye and to allow the eye to focus on near objects and maintain a clear image. In alternative approaches, presbyopia has been at least partially corrected by the use of bi-focal eyeglasses, where one portion of an eyeglass lens provides correction for distance vision, and another portion of the eyeglass lens provides correction for near vision. Thus, with little or no accommodation, the individual can see both far and near objects. Contact lenses and intra-ocular lenses (IOLs) have also been used to treat presbyopia. For example, individuals have been provided with monovision (where one eye is corrected for distance-vision, while the other eye is corrected for near-vision) or bilateral correction with either bi-focal or multi-focal lenses. Although the aforementioned treatments have provided relatively successful results for correcting presbyopia, many of the aforementioned treatments, such as those in which eyeglasses and contact lenses are employed, provide temporary solutions for the individual. Additionally, implantation of IOLs introduces non-corneal tissue matter into the eye and may be relatively costly to perform.

Recently, ablation procedures have been explored as possible treatment solutions for mitigating presbyopic conditions. For example, certain ablation profiles have been suggested for treating presbyopia, often with the goal of increasing the range of focus of the eye. However, the suggested ablation profiles have typically included ablation dimensions requiring the removal of a substantial amount of corneal tissue, precluding some presbyopic individuals from qualifying for the ablation procedures.

BRIEF SUMMARY

Methods and systems for treating presbyopia are provided.

In accordance with an embodiment, by way of example only, a method of treating presbyopia of an eye includes ablating the stroma to form a final ablated shape in the stroma, the final ablated shape including a central zone defined by a concavity having a central zone depth and a central zone diameter, the central zone depth and the central zone diameter each selected to provide the cornea with a near vision add power after the epithelium is regenerated over the stroma.

In another embodiment, by way of example only, a system for treating presbyopia includes a laser, a support, a processor, and a computer readable medium. The laser is configured to provide a laser beam along an optical path. The support is configured for positioning an eye for presbyopic treatment in the optical path of the laser beam. The processor is in operable communication with the laser. The computer readable medium includes instructions that, when executed, cause the processor to (1) determine a laser target surface on the eye and (2) provide commands to the laser to ablate a surface of the stroma to form a final ablated shape in the stroma, wherein the final ablated shape includes a central zone defined by a concavity having a central zone depth and a central zone diameter, and the central zone depth and the central zone diameter in combination provide the cornea with a near-vision add power after the epithelium is regenerated over the stroma.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

The inventive subject matter will hereinafter be described in conjunction with the following drawing figures, wherein like numerals denote like elements.

DETAILED DESCRIPTION

Figure 1:
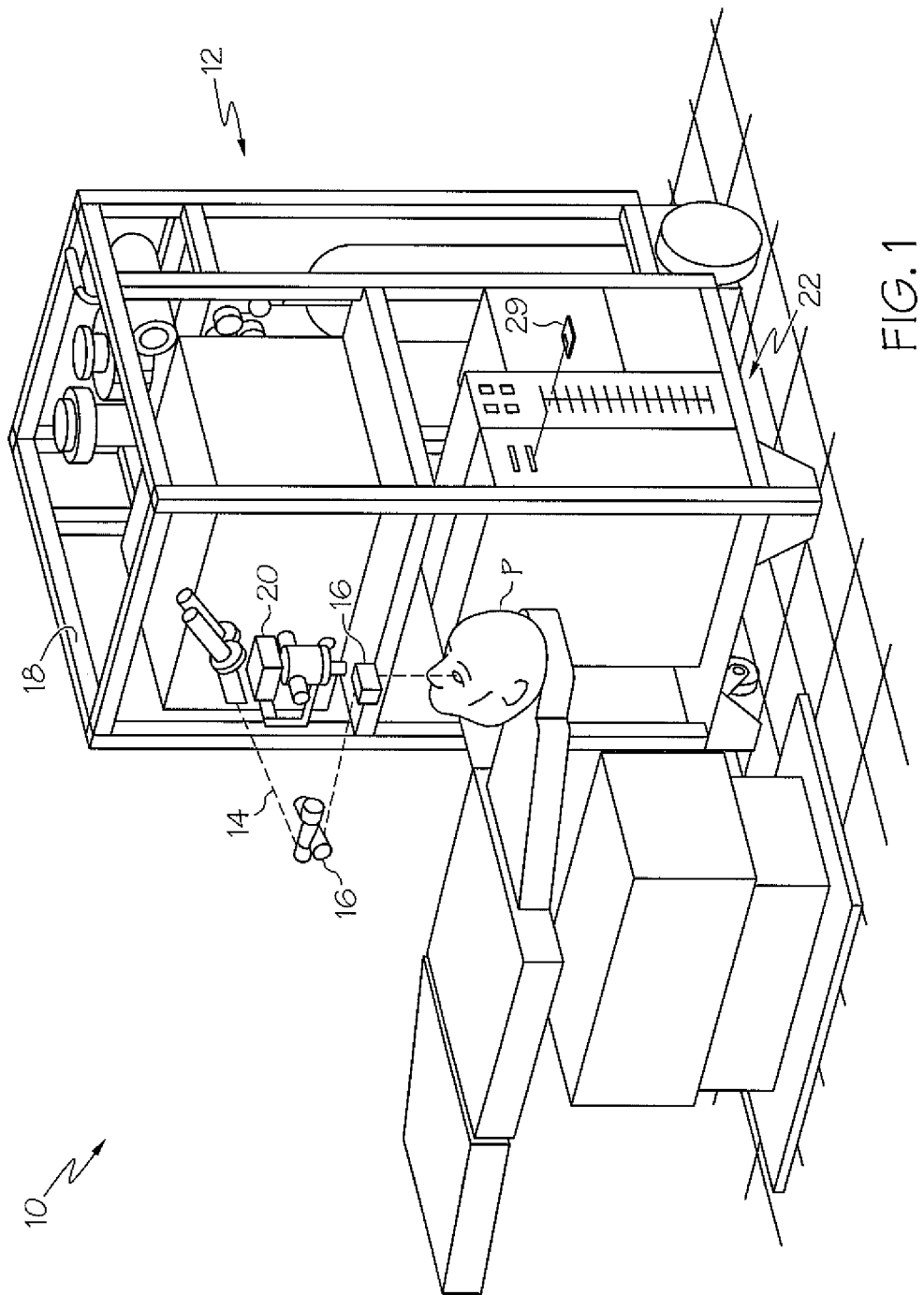
FIG. 1 is a perspective view of a simplified laser ablation system, according to an embodiment.

The following detailed description is merely exemplary in nature and is not intended to limit the inventive subject matter or the application and uses of the inventive subject matter. Certain terminology may also be used in the following description for the purpose of reference only, and thus are not intended to be limiting. For example, terms such as "anterior", "posterior", "inner", and "outer" may refer to directions in the drawings to which reference is made and/or the orientation or location of portions of the component within a consistent but arbitrary frame of reference which is made clear by reference to the text and the associated drawings describing the component under discussion. Such terminology may include the words specifically mentioned above, derivatives thereof, and words of similar import.

Generally, the inventive subject matter provides an improved method for treating presbyopia by ablating stromal tissue of an eye to a desired final ablated shape, where the final ablated shape provides a near vision add power to the eye after the epithelium regenerates over the ablated stromal tissue. The method is sufficiently robust for simple adjustment of the light energy distribution between near and distant vision. The method can be readily adapted for use with existing laser systems, wavefront measurement systems, and other optical measurement devices. While the systems, software, and methods of the inventive subject matter are described primarily in the context of a laser eye surgery system, the inventive subject matter may be adapted for use in combination with alternative eye treatment procedures and systems such as spectacle lenses, intraocular lenses, contact lenses, corneal ring implants, collagenous corneal tissue thermal remodeling, and the like, as well as in combination with pre-existing or planned ophthalmic therapies (e.g., laser assisted in situ keratomileusis (LASIK), photorefractive keratectomy (PRK), laser epithelial keratomileusis (LASEK), radial keratotomy (RK), keratoplasty, and the like). Furthermore, there is no intention to be bound by any theory presented in the preceding background or the following detailed description.

FIG. 1 is a perspective view of a simplified laser ablation system 10, according to an embodiment. The laser ablation system 10 may be employed to ablate an eye and includes a laser 12 that produces a laser beam 14. Laser 12 is optically coupled to laser delivery optics 16, which directs laser beam 14 to an eye of patient P. A delivery optics support structure (not shown here for clarity) extends from a frame 18 supporting laser 12. A microscope 20 is mounted on the delivery optics support structure, the microscope often being used to image a cornea of the eye.

Laser 12 generally comprises an excimer laser as a laser source. The excimer laser comprises an argon-fluorine laser producing pulses of laser light having a wavelength of approximately 193 nm. Laser 12 may provide a feedback stabilized fluence at the patient's eye, delivered via laser delivery optics 16. Alternative laser sources of ultraviolet or infrared radiation may be employed in other embodiment, particularly those adapted to controllably ablate the corneal tissue without causing significant damage to adjacent and/or underlying tissues of the eye. In alternate embodiments, the laser source employs a solid state laser source having a wavelength between 193 nm and 215 nm as described in U.S. Pat. Nos. 5,520,679 and 5,144,630 to Lin and 5,742,626 to Mead, the full disclosures of which are incorporated herein by reference. In another embodiment, the laser source is an infrared laser as described in U.S. Pat. Nos. 5,782,822 and 6,090,102 to Telfair, the full disclosures of which are incorporated herein by reference.

Laser 12 and laser delivery optics 16 will generally direct laser beam 14 to the eye of patient P under the direction of a computer system 22. Computer system 22 may be configured to selectively adjust laser beam 14 to expose portions of the cornea to the pulses of laser energy so as to effect a predetermined sculpting of the cornea and alter the refractive characteristics of the eye. In some embodiments, both laser 12 and laser delivery optics 16 will be under control of computer system 22 to effect the desired laser sculpting process, with the computer system effecting (and optionally modifying) the pattern of laser pulses. The pattern of pulses may be summarized in machine readable data of tangible media 29 in the form of a treatment table, and the treatment table may be adjusted according to feedback input into computer system 22 from an automated image analysis system (or manually input into the processor by a system operator) in response to real-time feedback data provided from an ablation monitoring system feedback system. Laser ablation system 10 and computer system 22 may continue and/or terminate a sculpting treatment in response to the feedback, and may optionally also modify the planned sculpting based at least in part on the feedback.

Additional components and subsystems may be included with laser ablation system 10, in an embodiment. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913; 4,669,466; 4,732,148; 4,770,172; 4,773,414; 5,207,668; 5,108,388; 5,219,343; 5,646,791; and 5,163,934, the complete disclosures of which are incorporated herein by reference. The Star family of laser systems by Abbott Medical Optics Inc. are an example of suitable excimer lasers. Other suitable systems include commercially available refractive laser systems such as those manufactured and/or sold by Alcon, Bausch & Lomb, Nidek, WaveLight, LaserSight, Schwind, Carl Zeiss Meditec, and the like. Femtosecond lasers may also be used to photoalter the epithelium, the stroma, or both the epithelium and stroma, and thereby remove corneal tissue in accordance with the invented subject matter. One advantage afforded by femtosecond laser photoalteration is the ability of subsurface stromal photoalterion without altering the epithelium interposed between the femtosecond laser and the desired stromal region for photoalteration. The FS60 or iFS™ laser systems by Abbott Medical Optics are examples of suitable femtosecond lasers, although other suitable systems include femtosecond laser systems such as those manufactured and/or sold by Ziemer Group, WaveLight, Technolas Perfect Vision, Carl Zeiss Meditec, and the like.

Figure 2:
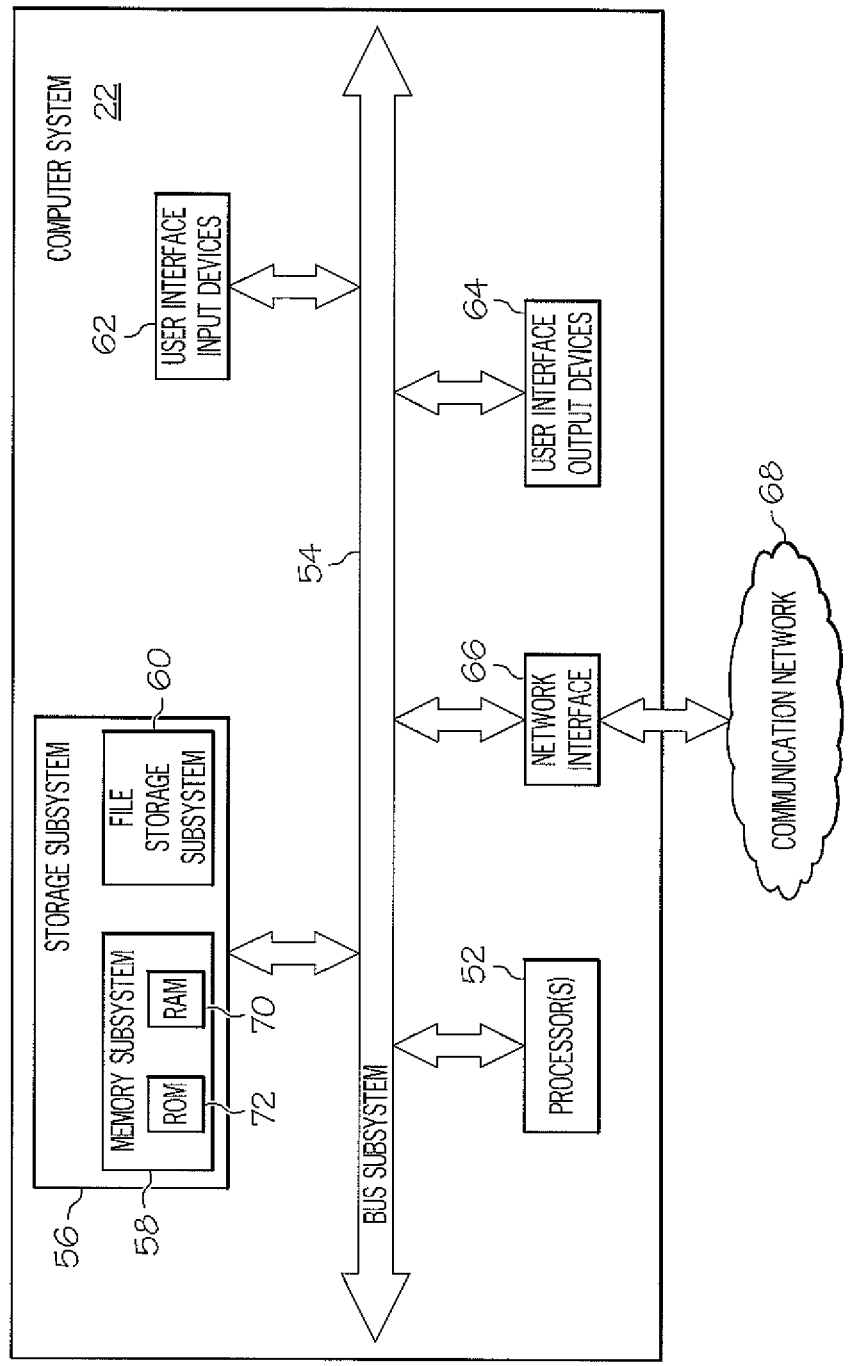
FIG. 2 is a simplified block diagram of a computer system, according to an embodiment.
Figure 3:
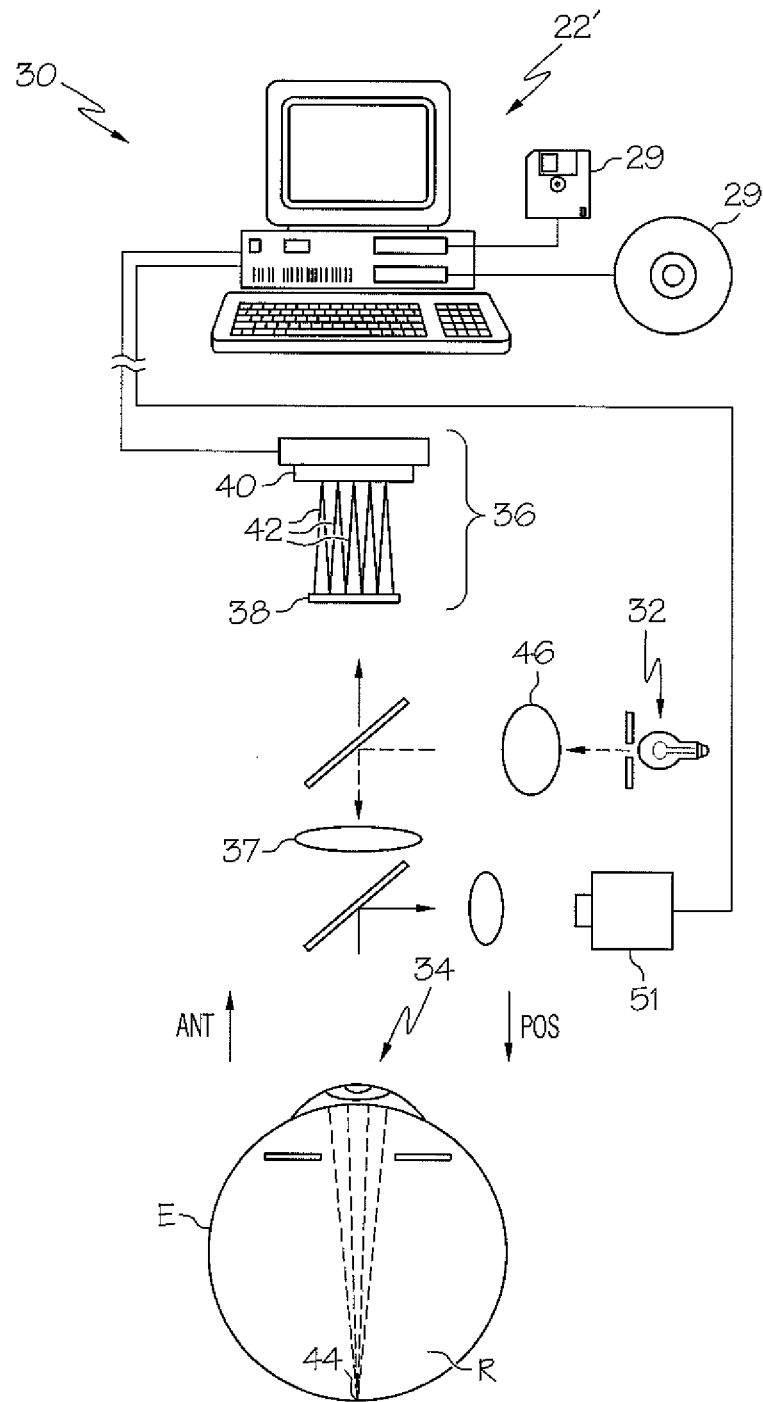
FIG. 3 is a simplified schematic of a wavefront measurement system, according to an embodiment.

FIG. 2 is a simplified block diagram of a computer system 22, according to an embodiment. Computer system 22 may be used by the laser ablation system 10 of FIG. 1 and may be employed to provide instructions to the laser ablation system 10 to ablate tissue from the eye to form a final ablated shape. In this regard, computer system 22 typically includes at least one processor 52 which may communicate with a number of peripheral devices via a bus subsystem 54. The peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as a wavefront measurement system 30 (FIG. 3).

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 may be used to download a computer executable code from a tangible media 29 embodying one or more methods disclosed herein. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 stores the basic programming and data constructs that provide the functionality of the various embodiments of the present invention. For example, a database and modules implementing the functionality of the methods of the present invention, as described herein, may be stored in storage subsystem 56. These software modules are generally executed by processor 52, which is suitably configured to perform various functions, tasks, and operations (described in more detail herein) in response to the execution of computer-readable instructions stored on tangible media. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a flash drive along with associated removable flash memory, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

In an embodiment, bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the inventive subject matter. Many other configurations of computer system 22 are possible having more or less components than the computer system depicted in FIG. 2.

FIG. 3 is a simplified schematic of wavefront measurement system 30, according to an embodiment. In accordance with an embodiment, wavefront measurement system 30 is configured to sense local slopes of a wavefront exiting the patient's eye. Devices based on the Hartmann-Shack principle generally include a lenslet array to sample the slopes across the pupil of the eye. Thereafter, the local slopes are analyzed so as to reconstruct the wavefront surface or map, often using Zernike polynomial expansion methods, which indicates ocular tissue aberrations.

According to an embodiment, one wavefront measurement system 30 includes a light source 32, such as a laser, which projects a source image through refractive tissues 34 of eye E so as to form an image 44 upon a surface of retina R. The image from retina R is transmitted by the refractive system of the eye (e.g., refractive tissues 34) and imaged onto a wavefront sensor 36 by system optics 37. Wavefront sensor 36 communicates signals to a computer system 22' for measurement of the optical errors in the optical tissues 34 and/or determination of an optical tissue ablation treatment program. Computer system 22' may include the same or similar hardware as the computer system 22 illustrated in FIGS. 1 and 2. Computer system 22' may be in communication with computer system 22 that directs laser ablation system 10, or some or all of the computer system components of the wavefront measurement system 30 and laser ablation system 10 may be combined or separate. If desired, data from wavefront sensor 36 may be transmitted to a laser computer system 22 via tangible media 29, via an I/O port, via a networking connection 66 such as an intranet or the Internet, or the like.

Wavefront sensor 36 generally comprises a lenslet array 38 and an image sensor 40. The reflected light from retina R is transmitted through optical tissues 34 and imaged onto a surface of image sensor 40 and the eye pupil P is similarly imaged onto a surface of lenslet array 38. The lenslet array separates the transmitted light beam into an array of beamlets 42, and (in combination with other optical components of the system) images the separated beamlets on the surface of sensor 40. Sensor 40 typically comprises a charge coupled device (CCD) and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Figure 4:
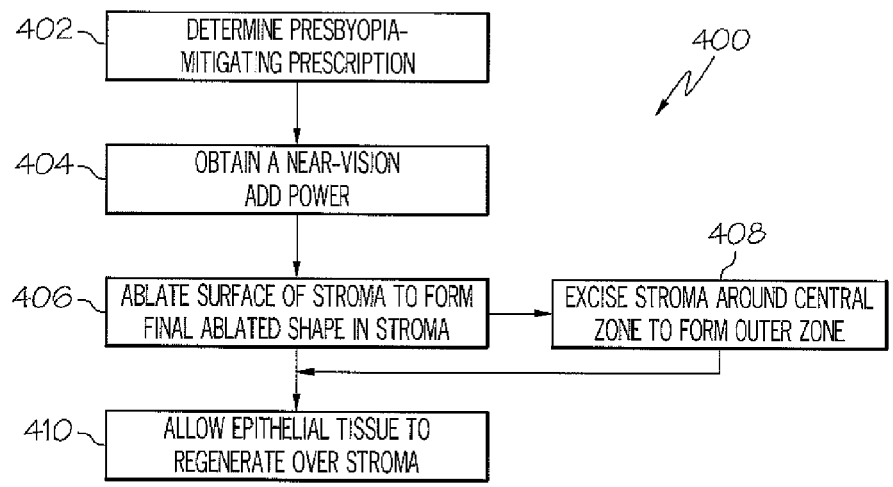
FIG. 4 is a flow diagram of a method of treating presbyopia, according to an embodiment.

Eye E generally defines an anterior orientation ANT and a posterior orientation POS. Light source 32 generally sends light in a posterior orientation through optical tissues 34 onto retina R as indicated in FIG. 4. Optical tissues 34 transmit light reflected from the retina anteriorly toward wavefront sensor 36. Image 44 actually formed on retina R may be distorted by any imperfections in the eye's optical system when the image source is originally transmitted by optical tissues 34. Optionally, image projection optics 46 may be configured or adapted to decrease any distortion of image 44.

In some embodiments, projection optics 46 may decrease lower order optical errors by compensating for spherical and/or cylindrical errors of optical tissues 34. Higher order optical errors of the optical tissues may also be compensated through the use of an adaptive optics system, such as a deformable mirror. Use of a light source 32 selected to define a point or small spot at image 44 upon retina R may facilitate the analysis of the data provided by wavefront sensor 36. Regardless of the particular light source structure, it will generally be beneficial to have a well-defined and accurately formed image 44 on retina R.

The wavefront data may be stored in computer readable medium 29 (FIG. 1) or a memory of wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 image. Such information may include all the available information on the wavefront error of the eye and is typically sufficient to reconstruct the wavefront or a desired portion of it. In such embodiments, there may be no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While embodiments of the inventive subject matter will generally be described with reference to sensing of an image 44, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles. In general, wavefront sensor data readings may be used in connection with the invented subject matter but are not necessarily required to provide near vision add power in accordance with the inventive subject matter. For example, wavefront sensor data readings provide details of refractive aberrations useful for developing a treatment plan to implement a refractive correction for an ametropic patient. Additionally, other aberrometers and/or topographers may be used with system 10. In some instances, a general determination of near vision acuity may be sufficient.

As noted above, the aforementioned systems 10, 30 may be employed in a method for treating presbyopia. FIG. 4 is a flow diagram of a method 400 of treating presbyopia, according to an embodiment. The various tasks performed in connection with method 400 may be performed by software, hardware, firmware, or any combination thereof. For illustrative purposes, the following description of method 400 may refer to elements mentioned above in connection with FIGS. 1-3. In practice, portions of the method 400 may be performed by different elements of the described system, e.g., laser ablation system 10, laser 12, computer system 22, processor 52 or wavefront system 30. It should be appreciated that the method 400 may include any number of additional or alternative tasks, the tasks shown in FIG. 4 need not be performed in the illustrated order, and the method 400 may be incorporated into a more comprehensive procedure or process having additional functionality not described in detail herein. Moreover, one or more of the tasks depicted in FIG. 4 may be omitted from a practical implementation (as long as the intended functionality and result is maintained).

In an embodiment, method 400 may include an initial step of determining a presbyopia-mitigating prescription, step 402. In accordance with an embodiment, step 402 may include determining whether an eye is ametropic. For example, a wavefront measurement system or another type of aberrometer may be employed to detect aberrations in a shape of the eye. If the eye is determined to be ametropic, a prescription is determined to correct the eye to emmetropia ("ametropic-correcting prescription"). Any one of numerous methods for determining the ametropic-correcting prescriptions may be employed. In one embodiment, measurements of a wavefront of an eye are obtained by the wavefront sensor system, and Zernike coefficients associated with the wavefront measurements are determined. The computer system calculates the ametropic-correcting prescription, based, in part, on the wavefront measurements and Zernike coefficients. Treatment according to the ametropic-correcting prescription generally leaves a treated eye with a desired shape to correct ametropic refractive errors.

In another embodiment of determining ametropic-correcting prescriptions, alternative methods may employ any of a variety of alternative mathematical frameworks so as to define the wavefront. For example, direct wavefront-based corneal ablation treatment prescriptions may be derived using methods and systems such as those described in U.S. patent application Ser. No. 10/006,992, the full disclosure of which is incorporated herein by reference. Wavefront reconstruction using Fournier transformations and direct integration may also be employed, including the techniques described in U.S. patent application Ser. No. 10/872,107, the full disclosure of which is also incorporated herein by reference. Regardless, the wavefront reconstruction will generally correspond to at least some amount of irregular aberration of the eye. By basing an ametropic-correcting prescription at least in part on such irregular aberrations, the ametropic-correcting treatments described herein may provide improved near-sighted visual acuities.

In some embodiments, other refractive eye surgeries may be performed concurrently with the presbyopia-correcting procedure. For example, in some cases, laser-assisted in situ keratomileusis or photorefractive keratectomy may be performed to correct myopia, hyperopia, and/or astigmatism. In these cases, wavefront measurements and/or other data for forming a topographical map of the patient's eye may be obtained before, concurrently with or after the presbyopia-mitigating prescription is determined to thereby provide prescriptions for at least 20/20 visual acuity or better than 20/20, along with presbyopia-mitigation. In some embodiments of method 400, an eye may be emmetropic, and step 402 may be omitted.

A desired near-vision add power is obtained for the eye, step 404. In an embodiment, step 404 may be performed before, after or in conjunction with determining the ametropic-correcting prescription of step 402. The near-vision add power may be obtained through eye chart testing of the patient or by another process. As used herein, the term "near-vision add power" (also referred to in the art as "near-vision plus power") may be defined as a difference in power between power required to provide near vision and the power required to focus light entering an unaccommodated eye from posterior to anterior of the eye in relation to the retina. As will be discussed in greater detail later, the near-vision add power is employed to determine a final ablated shape to be formed into the stroma. In an embodiment of step 404, a practitioner may prescribe the near-vision add power based on previous testing or experience.

Figure 5:
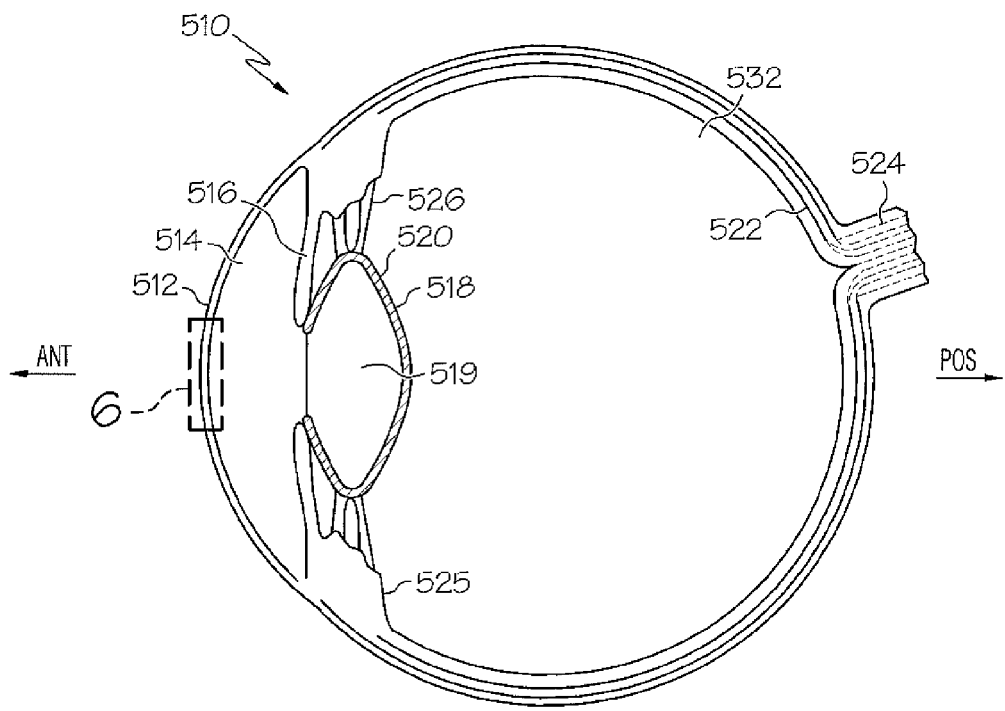
FIG. 5 is a cross-sectional diagram of a human eye, according to an embodiment.

In any case, after the desired near-vision add power is obtained, a surface of stroma is ablated to form a final ablated shape in stroma, step 406. For background, FIG. 5 is a cross-sectional diagram of a human eye 510. Light enters from the left of FIG. 5 (e.g., anterior (ANT) of eye 510), passes through a cornea 512, anterior chamber 514, and iris 516, and enters a capsular bag 518 (toward a posterior (PUS) area of eye 510. A crystalline lens 519 is located inside capsular bag 518, and crystalline lens 519 occupies essentially an entire interior of capsular bag 518. After passing through crystalline lens 519, light exits posterior wall 520 of capsular bag 518, passes through posterior chamber 532, and strikes retina 522, which detects the light and converts it to a signal transmitted through optic nerve 524 to the brain. A normal or well-corrected eye forms an image at retina 22. If the lens 519 has too much or too little power, the image shifts axially along the optical axis away from retina 22, toward or away from the lens.

Figure 6:
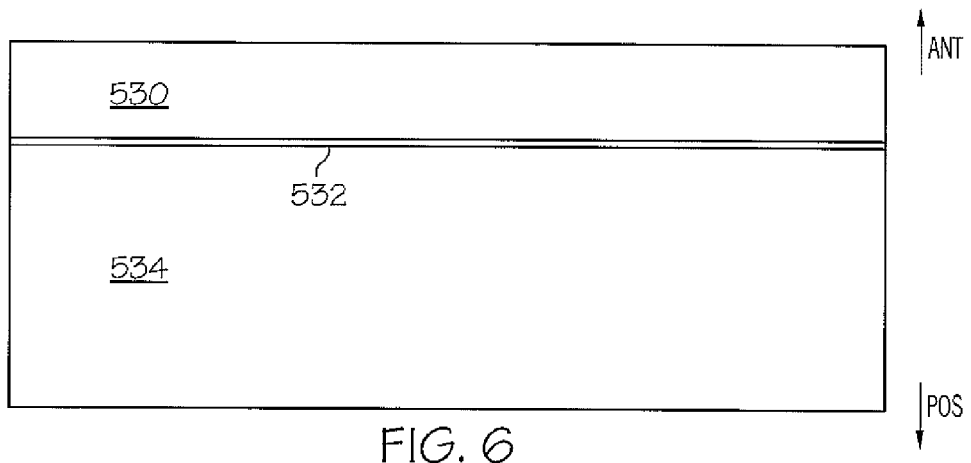
FIG. 6 is a close-up simplified cross-sectional view of a portion of cornea indicated by dotted box 6 in FIG. 5, according to an embodiment.

FIG. 6 is a close-up simplified cross-sectional view of a portion of cornea 512 indicated by dotted box 6 in FIG. 5, according to an embodiment. Cornea 512 comprises several layers and includes epithelial tissue 530, Bowman's layer 532, and stromal tissue 534. Epilthelial tissue 530 is located at an outermost portion of cornea 512 and comprises an anterior surface of eye 510. Bowman's layer 532 is disposed between epithelial tissue 530 and stromal tissue 534. Stromal tissue 534 forms a posterior portion of cornea 512.

As noted briefly above, a surface of stroma 534 is ablated to form a final ablated shape in the stroma 534. In one embodiment, initially, the epithelial tissue 530 is removed in order to expose a target surface of the stroma 534. For example, an excimer-type laser, a femto-second-type laser, or other mechanical means (i.e., a microkeratome-type of device) suitable for removing tissue may be employed to remove the epithelial tissue. According to an embodiment in which a laser system is employed, a processor (e.g., processor 52 of FIG. 2) provides commands to a laser ablation system (e.g., laser ablation system 10 of FIG. 2) according to instructions stored on computer readable medium (e.g., computer readable medium 29 of FIG. 2) to determine a laser target surface (e.g., a location on a cornea of the eye). The processor then provides commands to a laser (e.g., laser 12 of FIG. 2) to remove epithelial tissue from the laser target surface of the eye. In an embodiment, a selected portion of the epithelial tissue is completely removed from the eye. In alternative embodiments, the processor may provide commands to the laser to form a flap in the cornea at the laser target surface of the eye so that the flap (comprising epithelial tissue) is attached to the eye, but is separated from the anterior surface of the stroma.

Figure 7:
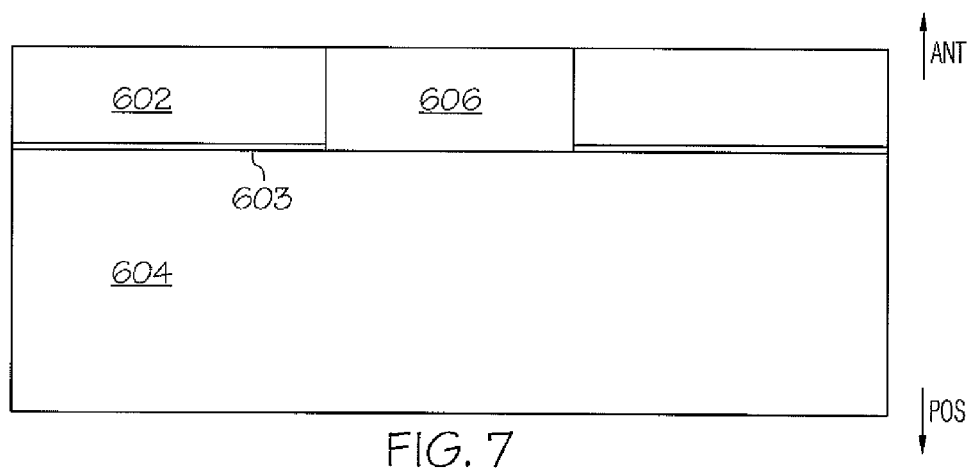
FIG. 7 is a simplified cross section of a cornea, where a portion of epithelium has been removed, according to an embodiment.

FIG. 7 is a simplified cross-sectional view of cornea 600, where a portion of epithelium 602 has been removed, according to an embodiment. The cornea 600, not drawn to scale, includes epithelial tissue 602, tissue comprising Bowman's layer 603, and stromal tissue 604. In an embodiment of step 404, epithelium 602 (and tissue comprising Bowman's layer 603) may be removed to form a space 606 over an anterior surface 608 of stroma 604. In an embodiment, space 606 may be cylindrical, frusto-conical, or another shape. In accordance with an embodiment, space 606 may have an average diameter in a range of about 1.0 mm to about 4 mm and an average depth in a range of about 0.005 mm to about 0.25 mm. In another embodiment, space 606 may have an average diameter that is about 2.4 mm and an average depth that is about 50 microns. In still other embodiments, space 606 may be larger or smaller than the aforementioned values and particular dimensions of space 606 may depend on an individual anatomy of the eye.

According to another embodiment, epithelial tissue is not removed before the stromal surface is ablated. For example, the femtosecond type laser may photoalter subsurface tissue of the epithelium and may be programmed to have a focal point located posterior to the epithelium in the stroma.

Figure 8:
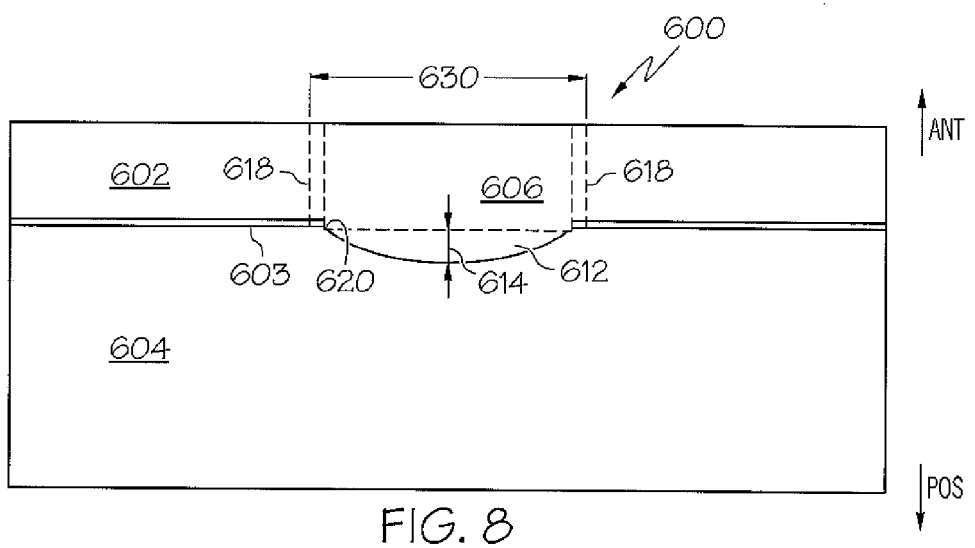
FIG. 8 is a simplified cross-sectional view of a cornea, where the portion of epithelium (shown in phantom) and a portion of stroma have been removed, according to an embodiment.
Figure 9:
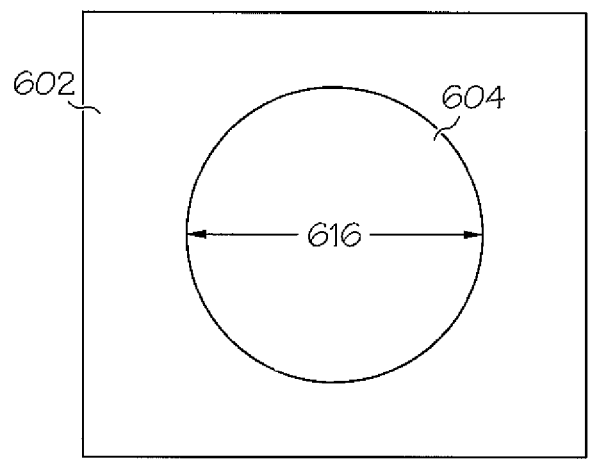
FIG. 9 is a front view of the cornea of FIG. 8, according to an embodiment.

In any case, as noted briefly above, the surface of stroma is ablated to form a final ablated shape in stroma. The processor provides commands to laser ablation system according to instructions stored on computer readable medium to determine a laser target surface on the eye (e.g., a location on the stroma) and provides commands to the laser to remove stromal tissue from the laser target surface on the eye. FIG. 8 is a simplified cross-sectional view of cornea 600, where the portion of epithelium 602 (shown in phantom) and a portion of stroma 604 have been removed, and FIG. 9 is a front view of the cornea 600 of FIG. 8, according to an embodiment. The ablation of stroma 604 forms the final ablated shape. In an embodiment, the final ablated shape includes a central zone 612 defined by a concavity having a central zone depth 614 (FIG. 8) and a central zone diameter 616 (FIG. 9). In accordance with an embodiment, the concavity of the final ablated shape in stroma 604 defines an anterior surface of the stroma 604. In addition to the central zone depth and diameter, the final ablated shape may have a particular radius of curvature. As used herein, the term "radius of curvature" may be identified as a curvature of an ablated surface of the stroma and defines the central zone 612. According to another embodiment, the concavity may comprise a portion of a concave shape, a portion of a frusto-conical, or a portion of another shape other than concave or frusto-conical defining the anterior surface of the stroma 604. In an embodiment, ablation of stroma 604 results in permanent removal of stromal tissue from the laser target surface of the eye. In this regard, the laser may be used to cut a portion of the stromal tissue in the final ablated shape and the cut tissue may be removed from the stroma 604. In another embodiment, such as in the embodiment in which an excimer- or femtosecond-type laser is employed, the laser may be used to vaporize tissue of the stroma, and the vaporized tissue may be off-gassed.

The central zone depth 614, the central zone diameter 616, and/or radius of curvature may be selected to provide the near-vision add power to the stroma 604 after the epithelium 602 is regenerated to thereby improve a patient's vision clarity. The central zone depth ("d"), central zone diameter ("D"), and radius of curvature ("R") of the central zone 612 are interrelated by the following equation [1]:

$$d = D^2 \div 8R \qquad [1]$$

The central zone diameter (D) may be calculated by using equation [2] as follows:

$$D = \Phi \sqrt{\%} \qquad [2]$$

where % represents an optimal percentage of light passing through a near vision zone of the cornea and Φ represents an average photopic pupil diameter of a patient who is 45 years or older.

The radius of curvature ("R") may be calculated by using equation [3] as follows:

$$R = \Delta n \div \Delta P \qquad [3]$$

where ΔP represents a desired near vision add power and Δn represents a difference in refractive index between the epithelium and stroma.

The central zone diameter D and radius of curvature R may be inputted into equation [1] above to obtain the central zone depth d.

According to an embodiment, it has been found that the optimal percentage of light passing through a near vision zone of the cornea (%) may be between about 20% to about 60%, and the average photopic pupil diameter of a patient who is 45 years or older (Φ) may be about 4 mm. Investigators have also shown that the difference in refractive index between the epithelium and stroma (Δn) is 0.0177 and that because the refractive index of the epithelium is higher then the refractive index of the stroma, an added refraction on an optical axis of the eye may result after corneal ablation. In any case, based on the aforementioned values and the equations [1]-[3] above, in an embodiment in which near-vision add power is in a range of about 1.5 Diopters to about 3.0 Diopters, the central zone depths may be in a range of about 10 microns to about 300 microns, the central zone diameters may be in a range of about 1.5 mm to about 3.5 mm, and the radii of curvature may be in a range of about 3.0 mm to about 20 mm.

In another embodiment in which a desired near-vision add power is 1.0 Diopter, the central zone diameter may be in a range of about 1.0 mm to 3.0 mm, and the central zone depth may be in a range of about 6 μm to about 50 μm. In still another embodiment in which the near-vision add power is 1.5 Diopter, the central zone diameter may be in a range of about 1.0 mm to 3.0 mm, and the central zone depth may be in a range of about 8 μm to about 75 μm. According to another embodiment in which a desired near-vision add power is 2.0 Diopter, the central zone diameter may be in a range of about 1.0 mm to 3.0 mm, and the central zone depth is in a range of about 11 μm to about 100 μm. In accordance with another embodiment, where a desired near-vision add power is 2.5 Diopter, the central zone diameter may be in a range of about 1.0 mm to 3.0 mm, and the central zone depth may be in a range of about 14 μm to about 125 μm. If a desired near-vision add power is 3.0 Diopter, the central zone diameter may be in a range of about 1.0 mm to 3.0 mm, and the central zone depth may be in a range of about 17 μm to about 180 μm, in an embodiment. In another embodiment in which a near-vision add power is 3.5 Diopter, the central zone diameter may be in a range of about 1.0 mm to 3.0 mm, and the central zone depth may be in a range of about 21 μm to about 210 μm.

Selection of one or both of the central zone diameter and/or depth may depend on certain factors. For example, selection of a particular central zone depth value may depend on an amount of corneal tissue that may be available for ablation, which may determine which corresponding central zone diameter may be selected.

With reference to FIG. 5, in an embodiment, the ablation profile provided by the processor may be associated with commands to form the final ablated shape such that it has smaller dimensions than space 606. In any case, an edge 620 defined between phantom walls 618 and central zone 612 may result around central zone 612, after stroma 604 is ablated. According to an embodiment, the edge 618 may be beveled or smooth and curved.

As alluded to above, in some embodiments, a patient's corneal tissue may not be suitable for ablation to the central zone depths noted above. In these cases, the final ablated shape may be formed to provide properties similar to those of a Fresnel lens. For example, a central zone may be formed according to steps 404 through 406 of method 400. However, the central zone may have a central zone diameter and a central zone depth that are less than the central zone diameter and a central zone depth of the aforementioned lenses described above.

Figure 10:
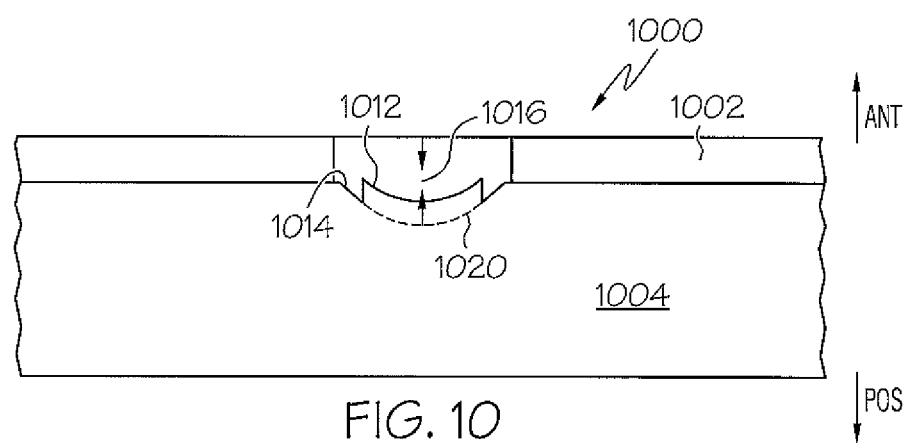
FIG. 10 is a simplified cross section of a cornea, where the portion of epithelium and a portion of stroma have been removed, according to another embodiment.
Figure 11:
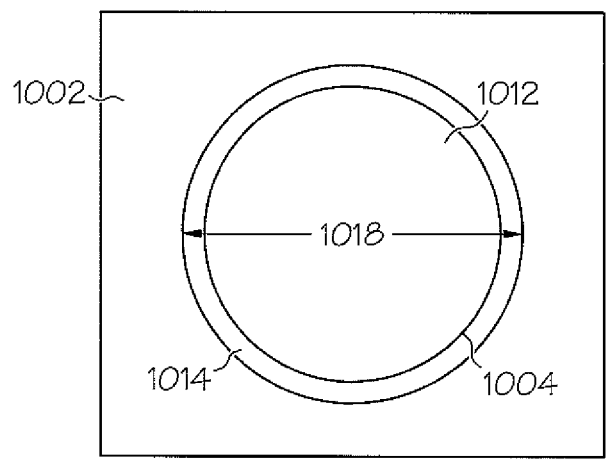
FIG. 11 is a front view of the cornea of FIG. 10, according to an embodiment.

To form the Fresnel lens, stroma 1004 around the central zone may be excised or vaporized to form a ring-shaped outer zone 1014, step 408. FIG. 10 is a simplified cross-sectional view of a cornea 1000, where a portion of epithelium 1002 and a portion of stroma 1004 have been removed leaving the final ablated shape in the stroma 1004, and FIG. 11 is a front view of the cornea 1000 of FIG. 10, according to an embodiment. In an embodiment, the ring-shaped outer zone 1014 has a shape that is substantially similar to an outer periphery of a concave shape, as shown in FIG. 11. Accordingly, ring-shaped outer zone 1014 may have an outer zone diameter 1018 and an outer zone depth 1016, which when employed in conjunction with the central zone 1012 provides the cornea with a desired near-vision add power after epithelium is regenerated over stroma 1004. The outer zone diameter 1018, as alluded to above, is greater than a diameter of central zone 1012. In some embodiments, the outer zone diameter 1018 may be substantially equal to one of the values provided above for the central zone diameter. In another embodiment, the outer zone diameter 1018 may be greater than the range of values provided above, while the diameter of central zone 1012 may fall within the ranges provided above.

In another embodiment, the outer zone depth 1016, measured at a deepest portion of the final ablated shape from an unablated anterior surface of the stroma 1004 to dotted line 1020, indicating a curvature of the ablated anterior surface of the stroma 1004, may be substantially equal to that of the central zone depth. Although a single ring-shaped outer zone is included in the embodiment depicted in FIGS. 10 and 11, more than one ring-shaped outer zone, each formed concentric to the central zone 1012, may be included in other embodiments. Generally for a Fresnel lens, the radii of curvature and depths are substantially equal for each of the central zone 1012 and outer zones, but the diameters of central zone ($D_1$), a first outer zone ($D_2$), a second outer zone ($D_3$), a third outer zone ($D_4$), etc. are not equal. Instead:

The diameter of the first outer zone $(D_2)=D_1*(2)^{0.5}$.
The diameter of the second outer zone $(D_3)=D_1*(3)^{0.5}$
The diameter of the third outer zone $(D_4)=D_1*(4)^{0.5}$, and so on for additional successive outer zone.

Although the ring-shaped outer zone 1014 is described above as being formed after the central zone 1012 (e.g., where step 408 occurs after step 406), the ring-shaped outer zone 1014 may be formed before the central zone 1012 (e.g., where step 408 occurs before step 406) in other embodiments.

In accordance with another embodiment, other refractive eye surgeries may be performed before or after the final ablated shape is formed in the stroma. For example, laser-assisted in situ keratomileusis or photorefractive keratectomy may be performed to thereby provide prescriptions for at least 20/20 visual acuity or better than 20/20.

After the final ablated shape has been formed into the stroma (and after the other refractive eye surgeries are performed, in some embodiments), epithelial tissue is allowed to regenerate over the stroma, step 410. According to an embodiment, epithelial regeneration may be accelerated by administering an eye wash over the cornea. The eye wash may include riboflavin or another suitable growth-promoting compound. In an embodiment, the epithelium regenerates to cover the stroma and to occupy space 606 (FIGS. 6 and 7) to thereby provide an original shape of the anterior surface of the eye. In embodiments in which a flap of epithelial tissue had been formed in the eye, the flap may be replaced over the stroma and epithelial regeneration may occur between the flap and the stroma.

EXAMPLE

Figure 12:
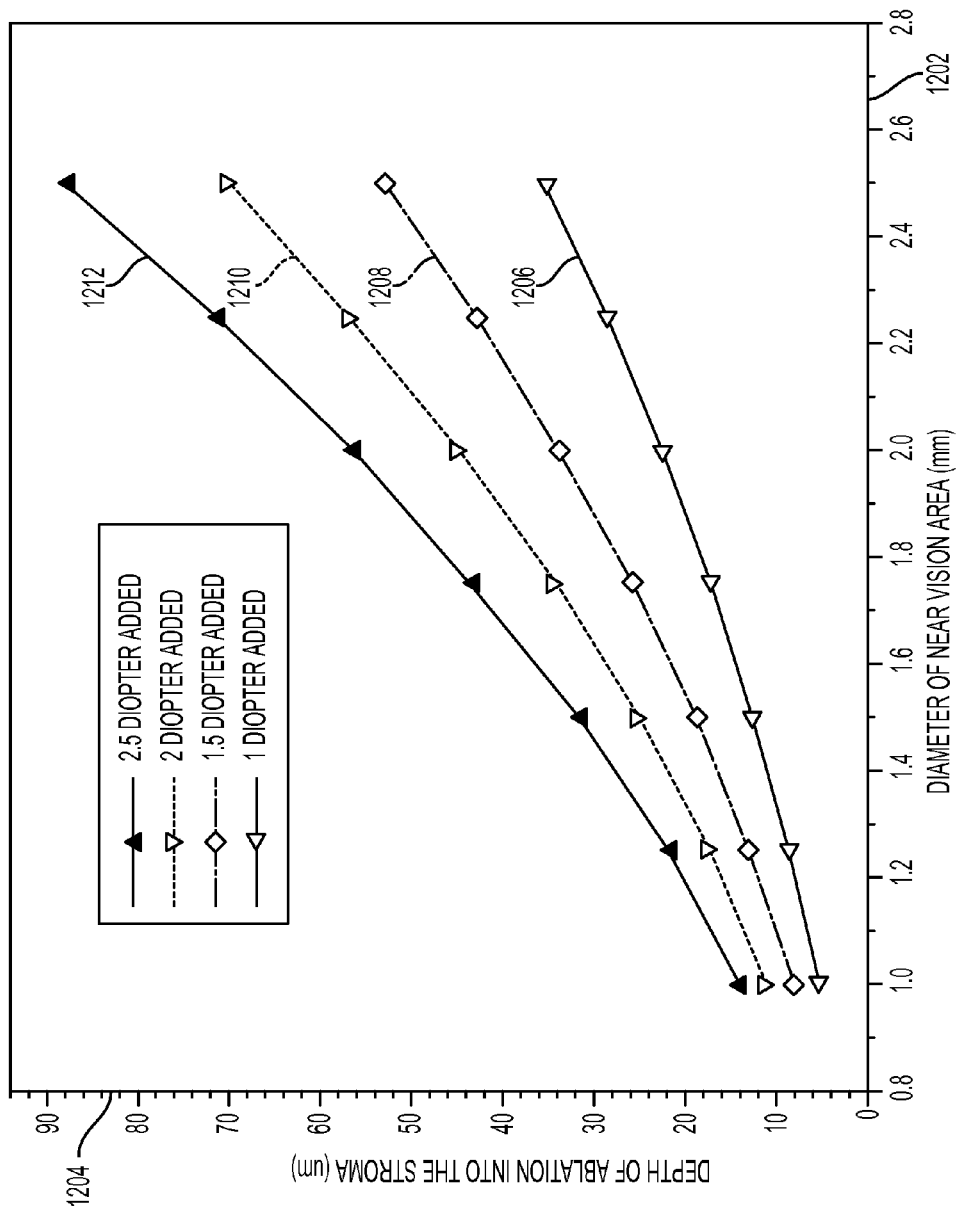
FIG. 12 is a graph showing an ablation profile for final ablated shapes for use in the method of FIG. 4, according to an embodiment.

FIG. 12 shows the calculated ablation depth as a function of the added lens diameter for 1, 1.5, 2 and 2.5 diopter added power. It has been discovered that the ablation profiles depicted in FIG. 12 may provide improved near visual acuity while allowing for easy adjustment of light energy distribution between near and distant vision. FIG. 12 includes X-axis 1202 depicting a central zone diameter of the final ablated shape and y-axis 1204 depicting a central zone depth of the final ablated shape. Four lines 1206, 1208, 1210, 1212 extend across the graph from a central zone diameter value of about 1.0 mm to a value of about 2.5 mm. Each line 1206, 1208, 1210, 1212 represents an near-vision add power of 1 Diopter, 1.5 Diopter, 2.0 Diopter, and 2.5 Diopter, respectively. Generally, to provide between 1 Diopter to 2.5 Diopter, the final ablated shape may have a central zone diameter in a range of about 1 mm to 2.5 mm and a central zone depth of in a range of about 6 μm to about 88 μm. According to an embodiment of method 400, typically, practitioners may determine that a patient may benefit optimally from an near-vision add power of 2.0 Diopter and a central zone diameter of about 2.0 mm. In such case, the central zone depth of the final ablated shape may be in a range of about 40 μm to about 50 μm. In other embodiments, the diameter and/or depth of the central zone may be greater or less than the aforementioned ranges.

To provide a 1 Diopter near-vision add power, the final ablated shape may have a central zone diameter in a range of about 1 mm to 2.5 mm and a central zone depth of in a range of about 6 μm to about 35 μm. According to another example, to provide a near-vision add power of 1.5 Diopter, the final ablated shape may have a central zone diameter in a range of about 1.0 mm to 2.5 mm and a central zone depth of in a range of about 8 μm to about 53 μm. In another embodiment, in order to provide an near-vision add power of 2.0 Diopter, the final ablated shape may have a central zone diameter in a range of about 1.0 mm to 2.5 mm and a central zone depth of in a range of about 11 μm to about 70 μm. In still another embodiment, to provide an near-vision add power of 2.5 Diopter, the final ablated shape may have a central zone diameter in a range of about 1.0 mm to 2.5 mm and a central zone depth of in a range of about 14 μm to about 88 μm.

After the procedure and after the eye is substantially healed, the patient may experience reduced vision problems associated with presbyopia. By modifying a shape of the stroma to thereby change a curvature of the anterior surface of stroma and a curvature of a posterior surface of the epithelium, the paths along which light traveling from the epithelium to the stroma is modified. Specifically, because a refractive index of the epithelium is higher than that of the stroma, the change in refractive index in combination with the changed curvatures causes the light to focus at a location on a lens posterior to the stroma, rather than at a location that is not on the lens. Consequently, improved visual acuity may result. Moreover, the above-described method of imparting a near-vision add power to the eye minimizes impact on an eye's intermediate and far vision by limiting a central zone diameter to be ablated into the stroma.

While at least one exemplary embodiment has been presented in the foregoing detailed description of the inventive subject matter, it should be appreciated that a vast number of variations exist. It should also be appreciated that the exemplary embodiment or exemplary embodiments are only examples, and are not intended to limit the scope, applicability, or configuration of the inventive subject matter in any way. Rather, the foregoing detailed description will provide those skilled in the art with a convenient road map for implementing an exemplary embodiment of the inventive subject matter. It being understood that various changes may be made in the function and arrangement of elements described in an exemplary embodiment without departing from the scope of the inventive subject matter as set forth in the appended claims.

What is claimed is:

1. A method of treating presbyopia of an eye, the method comprising:
    determining a presbyopia-correcting refractive power for the eye by determining an ametropic-correcting prescription for the eye; and
    ablating a stroma of a cornea of the eye to form a final ablated shape in the stroma, the final ablated shape including a central zone defined by a concavity having a central zone depth (d), a central zone diameter (D), and a radius of curvature (R) in a range of about 3 mm to about 20 mm, the central zone depth and the central zone diameter each selected to provide a near-vision add power between 1.0 Diopters and 3.5 Diopters after the epithelium is regenerated over the stroma; wherein $$d = D^2 \div 8R,$$

$D = \Phi \sqrt{\%}$, where % is an optimal percentage of light passing through a near vision zone of the cornea and (1) is an average photopic pupil diameter of a patient who is 45 years or older, the optimal percentage being between about 20% and about 60% and $R = \Delta n \div \Delta P$ where $\Delta P$ is a desired near vision add power and $\Delta n$ is a difference in refractive index between the epithelium and the stroma.

2. The method of claim 1, further comprising excising tissue from the stroma around the central zone to form a ring-shaped outer zone, the ring-shaped outer zone having an outer zone diameter and an outer zone depth, each selected to provide the cornea with the near-vision add power after the epithelium is regenerated.

3. The method of claim 1, wherein ablating the stroma results in the central zone having the central zone diameter in a range of about 1.5 millimeters to about 3.5 millimeters and having the central zone depth in a range of about 10 μm to about 300 μm.

4. The method of claim 1, wherein the near-vision add power is 1.0 Diopter, the central zone diameter is in a range of about 1.0 mm to 3.0 mm, and the central zone depth is in a range of about 6 μm to about 50 μm.

5. The method of claim 1, wherein the near-vision add power is 1.5 Diopter, the central zone diameter is in a range of about 1.0 mm to 3.0 mm, and the central zone depth is in a range of about 8 μm to about 75 μm.

6. The method of claim 1, wherein the near-vision add power is 2.0 Diopter, the central zone diameter is in a range of about 1.0 mm to 3.0 mm, and the central zone depth is in a range of about 11 μm to about 100 μm.

7. The method of claim 1, wherein the near-vision add power is 2.5 Diopter, the central zone diameter is in a range of about 1.0 mm to 3.0 mm, and the central zone depth is in a range of about 14 μm to about 125 μm.

8. The method of claim 1, wherein the near-vision add power is 3.0 Diopter, the central zone diameter is in a range of about 1.0 mm to 3.0 mm, and the central zone depth is in a range of about 17 μm to about 180 μm.

9. The method of claim 1, wherein the near-vision add power is 3.5 Diopter, the central zone diameter is in a range of about 1.0 mm to 3.0 mm, and the central zone depth is in a range of about 21 μm to about 210 μm.

10. The method of claim 1, further comprising the step of removing a portion of an epithelium of the cornea of the eye to expose an anterior surface of the stroma.

11. The method of claim 1, wherein ablating the stroma comprises photoaltering the stroma to expose a posterior surface of epithelium that is located anterior relative to the stroma.

12. A system for treating presbyopia of an eye having an epithelium, a cornea, and a stroma, the system comprising:
    a laser configured to provide a laser beam along an optical path;
    a support for positioning an eye for presbyopic treatment in the optical path of the laser beam;
    a processor in operable communication with the laser; and
    a computer readable medium including instructions that, when executed, cause the processor to (1) determine a laser target surface on the eye and (2) provide commands to the laser to ablate a surface of the stroma to form a final ablated shape in the stroma, wherein the final ablated shape includes a central zone defined by a concavity having a central zone depth (d), a central zone diameter (D), and a radius of curvature (R) in a range of about 3 mm to about 20 mm, and the central zone depth and the central zone diameter in combination provide the cornea with a near-vision add power between 1.0 Diopters and 3.5 Diopters after the epithelium is regenerated over the stroma; wherein $$d = D^2 \div 8R,$$

$D = \phi\sqrt{\%}$, where % is an optimal percentage of light passing through a near vision zone of the cornea and $\phi$ is an average photopic pupil diameter of a patient who is 45 years or older, the optimal percentage being between about 20% and about 60%, and $R = \Delta n \div \Delta P$, where $\Delta P$ is a desired near vision add power and $\Delta n$ is a difference in refractive index between the epithelium and the stroma.

13. The system of claim 12, wherein the computer readable medium comprises instructions that, when executed, cause the processor to provide commands to the laser to remove a portion of the epithelium to expose an anterior surface of the stroma.

14. The system of claim 12, wherein the computer readable medium comprises instructions that, when executed, cause the processor to provide commands to the laser to form a flap.

15. The system of claim 12, wherein the computer readable medium comprises instructions that, when executed, cause the processor to provide commands to the laser to excise tissue from the stroma around the central zone to form a ring-shaped outer zone, the ring-shaped outer zone having an outer zone diameter and an outer zone depth.

16. The system of claim 12, wherein the computer readable medium comprises instructions that, when executed, cause the processor to provide commands to the laser to excise tissue from the stroma to form the central zone having a central zone diameter in a range of about 1.0 millimeters to about 2.5 millimeters and a central zone depth in a range of about 0.6 μm to about 88 μm.

17. The system of claim 12, further comprising a wavefront measurement subsystem in operable communication with the processor, the wavefront measurement subsystem configured to generate wavefront data for one or more measured aberrations of the eye for use by the system to provide an ametropic-correcting prescription.

18. The system of claim 12, wherein the near-vision add power is 2.0 Diopter, the central zone diameter is in a range of about 1.0 mm to 3.0 mm, and the central zone depth is in a range of about 11 μm to about 100 μm.

19. The system of claim 12, wherein the near-vision add power is 2.5 Diopter, the central zone diameter is in a range of about 1.0 mm to 2.5 mm, and the central zone depth is in a range of about 14 μm to about 125 μm.

\* \* \* \* \*